US007875300B2

(12) United States Patent
Raskin et al.

(10) Patent No.: US 7,875,300 B2
(45) Date of Patent: Jan. 25, 2011

(54) METHODS FOR REDUCING CIRCULATING GLUCOSE LEVELS

(75) Inventors: Ilya Raskin, Manalapan, NJ (US); Nebojsa Ilic, Highland Park, NJ (US); Peter Kuhn, Colonia, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 544 days.

(21) Appl. No.: 11/604,082

(22) Filed: Nov. 24, 2006

(65) Prior Publication Data

US 2008/0124412 A1 May 29, 2008

(51) Int. Cl.
A61K 36/00 (2006.01)
(52) U.S. Cl. ..................................... 424/725
(58) Field of Classification Search .................. None
See application file for complete search history.

(56) References Cited

U.S. PATENT DOCUMENTS

| 5,879,682 | A | 3/1999 | Allas et al. | |
|---|---|---|---|---|
| 2005/0058728 | A1* | 3/2005 | Randolph et al. | 424/732 |
| 2005/0260290 | A1* | 11/2005 | Raskin et al. | 424/756 |
| 2006/0188590 | A1* | 8/2006 | Ono | 424/756 |

FOREIGN PATENT DOCUMENTS

| JP | 2006-045210 | * | 2/2006 |
| JP | 2006-249064 | * | 9/2006 |
| WO | WO-2005/025586 A1 | | 3/2005 |
| WO | WO-2005/074959 A1 | | 8/2005 |

OTHER PUBLICATIONS

Sekiya et al. BioFactors. 2004. vol. 22, No. 1-4, pp. 153-156.*
Kadnur et al. Indian J. Exp. Biol. Dec. 2005. vol. 43, No. 12, pp. 1161-1164, ESBIOBASE Abstract enclosed.*
Saeed et al. Intl. J. Biol. Biotechnol. Jul. 2006. vol. 3, No. 3, pp. 519-526, BIOSIS Abstract enclosed.*
Kato et al. J. Agric. Food Chem. 2006. vol. 54, No. 18, pp. 6640-6644.*
Shishodia et al. Annals New York Acad. Sciences. 2005. pp. 206-217, editor Kotwal, GJ, BIOSIS Abstract enclosed.*
Agricultural Research Service, "Phytochemical and Ethnobotanical Databases," Aframomum melegueta K., Schum.—Zingiberaceae Retrieved from the Internet on Apr. 5, 2004: <URL: http://www.ars-grin.gov:8080/npgspub/xsql/duke/plantdisp.xsql?taxon=2367>.
Baynes, "Role of Oxidative Stress in Development of Complications in Diabetes," Diabetes, 40:405-412 (1991).
Chung et al., "Antioxidative and Antitumbr Promoting Effects of [6]-paradol and its Homologs," Mutat. Res., 496:199-206 (2001).
Enyikwola, "Effects of Guinea Pepper (Aframomum melegueta) on Gastric Acid Secretion in Albino Rats," Int. J. Pharmacog., 32(1):37-43 (1994).
Giugliano etal., "Oxidative Stress and Diabetic Vascular Complications," Diabetes Care, 19(3):257-267 (1996).

Grundy et al., "Definition of Metabolic Syndrome: Report of the National Heart, Lung, and Blood Institute/American Heart Association Conference on Scientific Issues Related to Definition," Circulation, 109:433-438 (2004).
Guh et al., "Antiplatelet Effect of Gingerol Isolated from Zingiber officinale," J. Pharm. Pharmacol., 47:329-332 (1995).
ITIS Report, "Aframomum melegueta Schumann, Taxonomic Serial No. 506501," Retrieved from the Internet on Feb. 22, 2007: <URL: www.itis.gov/servlet/SingleRpt/SingleRpt>.
Iwu et al., "New Antimicrobials of Plant Origin," Perspectives on New Crops and New Uses, pp. 457-462, J. Janick (ed.), ASHS Press, Alexandria, VA (1999).
Iwu, African Ethnomedicine, Printed by CECTA (Nigeria) Limited, Enugu, Nigeria, Table of Contents, pp. 34-37, 62-65, and 70-71 (1986).
Iwu, Handbook of African Medicinal Plants, CRC Press, Inc., Boca Raton, Florida, Table of Contents, pp. 9-71 and 108-109 (1993).
Konning et al., "Antimicrobial Activity of Some Medicinal Plants from Ghana," Fitoterapia, 75:65-67 (2004).
Koo et al., "Gingerols and Related Analogues Inhibit Arachidonic Acid-induced Human Platelet Serotonin Release and Aggregation," Thromb. Res., 103:387-397 (2001).
Nurtjahja et al., "The Anti-platelet Aggregating Activity of Natural Ginger Constituents and Synthetic Analogues," $3^{rd}$ College of Health Sciences and Medical Foundation Research Conference: From Cell to Society 3, (Sep. 2002).
Nurtjahja-Tjendraputra et al., "Effective Anti-platelet and COX-1 Enzyme Inhibitors from Pungent Constituents of Ginger," Thromb. Res., 111:259-265 (2003).
Rafatullah et al., "Gastric and Duodenal Antiulcer and Cytoprotective Effects of Aframomum melegueta in Rats," Int. J. Pharmacog., 33(4):311-316 (1995).
Suekawa et al., "Pharmacological Studies on Ginger. I. Pharmacological Actions of Pungent Constituents, (6)-Gingerol and (6)-Shogaol," J. Pharm. Dyn., 7:836-848 (1984).
Surh, "Anti-tumor Promoting Potential of Selected Spice Ingredients with Antioxidative and Anti-inflammatory Activities: A Short Review," Food and Chem. Toxicol., 40:1091-1097 (2002).
Tackie et al., "Hydroxyphenylalkanones From Amomum melegueta," Phytochemistry, 14:853-854 (1975).
Tjendraputra et al., "Effect of Ginger Constituents and Synthetic Analogues on Cyclooxygenase-2 Enzyme in Intact Cells," Bioorg. Chem., 29:156-163 (2001).
U.S. Department of Agriculture, Natural Resources Conservation Service, Plants Classification Report, "Classification for Kingdom Plantae Down to Species Aframomum melegueta," Retrieved from the Internet on Apr. 5, 2004: <URL: http://plants.usda.gov/classification/output_report.cgi?3/S/AFME/u/140/+31>.

(Continued)

Primary Examiner—Christopher R. Tate
(74) Attorney, Agent, or Firm—Marshall, Gerstein & Borun LLP

(57) ABSTRACT

The invention relates to methods of reducing circulating glucose levels with compositions obtained from botanical sources. More specifically, the invention relates to methods of treating individuals whom wish to reduce their circulating glucose levels, particularly individuals having elevated circulating glucose levels, with an extract product of Aframomum melegueta.

10 Claims, No Drawings

OTHER PUBLICATIONS

Umukoro et al., "Effects of *Aframomum meleguta* Seed Extract on Thermal Pain and Carrageenin-Induced Oedema," *Nig. Ot J. Hosp. Med.*, 11(1-4):33-35 (2001).

Al-Amin et al., "Anti-Diabetic and Hypolipidaemic Properties of Ginger (*Zingiber officinale*) in Streptozotocin-Induced Diabetic Rats," *British J. Nutri.*, 96:660-666 (2006).

International Search Report for PCT/US2007/085369, dated May 22, 2008.

Written Opinion of the International Search Authority for PCT/US2007/085369, dated May 22, 2008.

International Preliminary Report on Patentability for PCT/US2007/085369, dated Jun. 4, 2009.

* cited by examiner

METHODS FOR REDUCING CIRCULATING GLUCOSE LEVELS

FIELD OF THE INVENTION

The invention relates to methods of reducing circulating glucose levels with compositions obtained from botanical sources. More specifically, the invention relates to methods of treating individuals whom wish to reduce their circulating glucose levels, particularly individuals having elevated circulating glucose levels (hyperglycemia), with an extract product of *Aframomum melegueta*.

BACKGROUND OF THE INVENTION

In most healthy individuals, the maintenance of blood glucose is a carefully regulated metabolic event. Glucagon, the 29-amino acid peptide responsible for maintaining blood glucose levels, increases glucose release from the liver by activating hepatic glycogenolysis and gluconeogenesis. When elevated blood glucose levels are present in an individual, insulin reverses the glucagon-mediated enhancement of glycogenolysis and gluconeogenesis. In some individuals, however, elevated glucose levels detrimentally persist for extended periods.

Such elevated glucose levels are most often associated with diabetes mellitus, a disease characterized by elevated glucose levels resulting from either an inability to produce insulin (Type I diabetes) or insulin resistance, i.e., the produced insulin is not sufficiently active in the individual (Type II diabetes) such that a given concentration of insulin produces a less-than-expected biological effect.

The key to diabetes treatment is to control circulating blood glucose levels within generally acceptable limits. Thus, diabetes treatment has traditionally focused on increasing insulin levels by injection, or alternatively, using oral agents to control blood glucose levels. Oral agents capable of controlling blood glucose levels include over-the-counter medications (e.g., metformin) and compositions derived from natural products, for example, compositions comprising plant extracts.

Type II diabetes (or non-insulin dependent diabetes) is often accompanied by metabolic syndrome. Metabolic syndrome is not a disease state per se, but rather the collective presence in an individual of risk factors such as abdominal obesity, atherogenic dyslipidemia, raised blood pressure, insulin resistance, glucose intolerance, proinflammatory conditions, and prothrombotic conditions [Grundy, et al., Circulation, 109(3):433-8 (2004)]. When one or more (particularly, three or more) of such risk factors is present, the individual has an increased risk for a variety of disease states including diabetes, heart disease, and/or stroke. Individuals having metabolic syndrome are also susceptible to other conditions such as polycystic ovary syndrome, fatty liver, cholesterol gallstones, asthma, sleep disturbances, and some forms of cancer. Thus, individuals suffering from type II diabetes are often obese and/or susceptible to hypertension (cardiovascular problems), in addition to having insulin resistance and/or elevated glucose levels.

Elevated glucose levels can also be present in individuals who are considered to have "pre-diabetes," a condition in which an individual's blood glucose levels are elevated, but not as much as individuals having diabetes.

Glucose levels are generally determined by using a Fasting Plasma Glucose Test (FPG) or an Oral Glucose Tolerance Test (OGTT), but other tests may also be used. With the FPG test, a fasting blood glucose level between 100 and 125 milligrams per deciliter (mg/dL) is indicative of pre-diabetes, and a fasting blood glucose level of 126 mg/dL or higher is indicative of diabetes. With the OGTT test, an individual's blood glucose level is measured two hours after drinking a glucose-rich beverage. A two-hour blood glucose level between 140 and 199 mg/dL is indicative of pre-diabetes, and a two-hour blood glucose level at 200 mg/dL or higher is indicative of diabetes.

Studies demonstrate that several biochemical pathways associated with elevated glucose levels can increase the production of free radicals [Giugliano, et al., Diabetes Care, 19:257-67 (1996)]. Free radicals generated by the autoxidation reactions of sugar and sugar adducts to proteins are possible sources of oxidative stress in patients with elevated glucose levels. Further, glycoxidation products accumulate in tissue collagen at an accelerated rate in patients with elevated glucose levels [Baynes, Diabetes, 40:405-12 (1991)]. Oxidative stress leads to complications including tissue damage and cell death. Thus, individuals having such elevated glucose levels have increased risks for heart disease (cardiovascular disease), blindness (retinopathy), nerve damage (neuropathy), kidney damage (nephropathy), and other conditions. In view of the foregoing, compositions that lower glucose levels are significant for health and wellness in general.

SUMMARY OF THE INVENTION

The invention provides methods for reducing circulating glucose levels with compositions obtained from botanical sources. Specifically, the invention provides methods for reducing circulating glucose levels comprising administering a therapeutically effective amount of a composition comprising a hypoglycemic extract product of an *Aframomum melegueta* plant to an individual desirous of having a reduced circulating glucose level. Methods and compositions in accordance with the invention have been used to measurably and safely reduce circulating glucose levels.

Advantageously, the disclosed botanical compositions are derived from easily cultivatable plants of the species *Aframomum melegueta*, also known as guinea pepper, alligator pepper, grains of paradise, and *Amomum melegueta*. In one embodiment, the compositions include an extract product of an *Aframomum melegueta* plant. The compositions may further comprise at least one formulation agent selected from the group consisting of diluents, fillers, salts, binders, and biologically acceptable carriers.

The invention also provides an article of manufacture comprising a hypoglycemic composition comprising an extract product of a plant material of an *Aframomum melegueta* plant, and a set of instructions for administering the composition to treat or prevent elevated glucose levels. Further, the invention provides for use of a composition comprising an extract product of a plant material of an *Aframomum melegueta* plant in the manufacture of a medicament for treating or preventing elevated glucose levels.

DETAILED DESCRIPTION OF THE INVENTION

The invention demonstrates that compositions comprising an extract product of *Aframomum melegueta* possess significant hypoglycemic activity, and thus are capable of measurably decreasing circulating glucose levels in an individual. The botanical compositions can be administered to an individual to treat a condition involving elevated blood glucose levels, for example, including but not limited to Type I diabetes, Type II diabetes, pre-diabetes, gestational diabetes, and other conditions involving elevated glucose levels. Further, the compositions can be administered prophylactically, e.g., to individuals who have a family history of diabetes or have other risk factors for developing such disease.

The compositions may be formulated as pharmaceutical compositions (e.g., an ethical drug), nutraceutical compositions (e.g., a dietary supplement), cosmeceuticals (e.g., a cosmetic product having biologically active ingredients), or as a food or beverage additive as defined by the U.S. Food and Drug Administration.

As used herein, the term "extract product" refers to any compound, any agent and/or mixtures thereof, that is obtained, isolated, and/or derived from an extract of a plant material. The term "plant material" refers to any plant material including, but not limited to, leaves, stems, flowers, fruits, seeds, roots, and combinations thereof.

The compositions in accordance with the invention advantageously comprise an extract product of *Aframomum melegueta*, an easily cultivatable, edible, agricultural crop. *Afromomum melegueta*, also known as guinea pepper, alligator pepper, grains of paradise, and *Amomum melegueta*, Roskoe, is a plant of West African origin. Ethnobotanically, the plant seeds have been chewed on cold days to 'promote' body warmth, and also have been extensively used as a food spice.

The compositions are generally administered to treat individuals having a fasting blood glucose greater than about 100 milligrams per deciliter (mg/dL) or greater than about 125 mg/dL, as measured by the FPG test. The compositions may also be used prophylactically, e.g., to treat individuals having fasting blood glucose greater than about 80 mg/dL, or greater than about 90 mg/dL, as measured by the FPG test, particularly when family history indicates an increased risk of developing diabetes (Type I or Type II), pre-diabetes, or gestational diabetes. Further, administration of the compositions may be warranted for individuals having moderately high glucose levels (e.g., greater than about 80 mg/dL, or greater than about 90 mg/dL, as measured by the FPG test) when one or more risk factors for CVD or metabolic syndrome including but not limited to abdominal obesity, raised blood pressure, atherogenic dyslipidemia (e.g., abnormal cholesterol or high triglycerides), proinflammatory conditions, and prothrombotic conditions is present. Such prophylactic treatment is particularly warranted when three or more of family history indicating an increased risk of developing diabetes (Type I or Type II), pre-diabetes, or gestational diabetes and the aforementioned risk factors are present.

Similarly, the compositions can be administered to treat individuals having a two-hour blood glucose level greater than about 140 mg/dL or greater than about 200 mg/dL, as measured by the OGTT test. The compositions may also be used prophylactically, e.g., to treat individuals having fasting blood glucose greater than about 120 mg/dL, or greater than about 130 mg/dL, as measured by the OGTT test, particularly when family history indicates an increased risk of developing diabetes (Type I or Type II), pre-diabetes, or gestational diabetes. Further, administration of the compositions may be warranted for individuals having moderately high glucose levels (e.g., glucose levels greater than about 120 mg/dL, or greater than about 130 mg/dL, as measured by the OGTT test) when one or more risk factors for CVD or metabolic syndrome including but not limited to abdominal obesity, raised blood pressure, atherogenic dyslipidemia (e.g., abnormal cholesterol or high triglycerides), proinflammatory conditions, and prothrombotic conditions is present. Such prophylactic treatment is particularly warranted when three or more of family history indicating an increased risk of developing diabetes (Type I or Type II), pre-diabetes, or gestational diabetes and the aforementioned risk factors are present.

Thus, the methods in accordance with the invention contemplate administration of an *Aframomum melegueta* extract product containing composition whether or not diabetic or pre-diabetic symptoms are manifest, i.e., prophylactic administration is contemplated.

In one aspect, the invention provides methods of treating individuals having elevated glucose levels comprising administering a therapeutically effective amount of a composition comprising an extract product of a plant material of an *Aframomum melegueta* plant to an individual having an elevated glucose level, or to an individual at risk of developing an elevated glucose level. It is contemplated that reducing elevated glucose levels and/or moderately high glucose levels will be beneficial because, e.g., the chronic damage caused to cell tissues caused by oxidative stress can be mitigated.

Thus, in one embodiment, the term "therapeutically effective amount" refers to an amount of a composition comprising an *Afromomum melegueta* extract product that is sufficient to reduce or decrease glucose levels in an individual. In an alternative embodiment, the term "therapeutically effective amount" refers to an amount of a composition comprising a hypoglycemic extract product that is sufficient to alleviate, ameliorate, prevent, and/or eliminate at least one pathology involving or associated with conditions involving elevated glucose levels.

Generally, the condition is selected from the group consisting of Type I diabetes, Type II diabetes, pre-diabetes, and gestational diabetes, and the pathology beneficially effected is selected from the group consisting of CVD risk factors or metabolic syndrome risk factors including but not limited to abdominal obesity, raised blood pressure, atherogenic dyslipidemia (e.g., abnormal cholesterol or high triglycerides), proinflammatory conditions, and prothrombotic conditions are present. Thus, in one aspect, the individual has at least one risk factor selected from the group consisting of abdominal obesity, atherogenic dyslipidemia, raised blood pressure, proinflammatory conditions, and prothrombotic conditions.

As used herein, "abdominal obesity" refers to an individual having an increased waist circumference, and typically is present in a human male having a waist greater than about 40 inches and in a human female having a waist greater than about 35 inches. In an alternative aspect, abdominal obesity refers to individuals with body mass indices (i.e., [(individual's weight in pounds)/(individual's height in inches)$^2$ times 703]) exceeding about 25, more typically more than about 30.

"Raised blood pressure" refers to an individual having a systolic pressure exceeding about 130 mm Hg and/or a diastolic pressure exceeding about 85 mm Hg.

"Atherogenic dyslipidemia" refers to an elevated triglyceride concentration (serum concentration $\geq 150$ mg/dL) and/or a depressed high-density lipoprotein cholesterol concentration (serum concentration $\leq 40$ mg/dL for a male or $\leq 50$ mg/dL for a female) in an individual.

As used herein, "proinflammatory conditions" refer to elevated concentrations of C-reactive protein, and "prothrombotic conditions" refer to increased plasminogen activator inhibitor (PAI)-1 and fibrinogen levels relative to healthy individuals, as is generally known. For example, administration of the compositions according to the invention can reduce various inflammatory markers including but not limited to Interleukin-6 (IL-6), Interleukin-8 (IL-8), and C-reactive protein (CRP), which are thought to have important interrelationships with traditional cardiovascular risk factors. Thus, individuals having family history indicating an increased risk of developing both cardiovascular disease and conditions involving elevated glucose levels stand to benefit from treatment in accordance with the invention.

Because preferred dosages of a number of oral medications for decreasing elevated glucose levels (including but not limited to metformin) are known in the art for a variety of therapeutic and prophylactic purposes, appropriate dosages of the appetite-suppressing compositions in accordance with the invention may be easily determined by standard methods.

As demonstrated herein, extract products obtained from *Aframomum melegueta* plants include compounds and/or agents capable of reducing elevated glucose levels in an individual. The hypoglycemic activity of *Aframomum melegueta* extract products (and thus, the disclosed hypoglycemic compositions) is generally attributed to the presence of one or more compounds in accordance with the following formula (I):

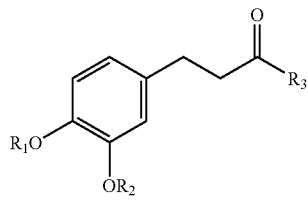

(I)

wherein $R_1$ is hydrogen or a $C_1$-$C_4$ moiety;
$R_2$ is hydrogen or a $C_1$-$C_4$ moiety; and,
$R_3$ is a $C_1$-$C_{10}$ moiety.

As used herein, the term "$C_1$-$C_4$ moiety" includes from one to four carbon atoms. Carbon-carbon bonds may be saturated or unsaturated. Non-carbon atoms may be bound to the carbon backbone, either directly or indirectly. Typical examples include alkyl, alkylene, heteroalkyl, and alkenyl groups as defined herein.

As used herein, the term "$C_1$-$C_{10}$ moiety" includes from one to ten carbon atoms. Carbon-carbon bonds may be saturated or unsaturated. Non-carbon atoms may be bound to the carbon backbone, either directly or indirectly. Typical examples include alkyl, alkylene, heteroalkyl, and alkenyl groups as defined herein.

"Alkyl" as used herein includes straight chain and branched hydrocarbon groups. "Alkylene" as used herein refers to alkyl groups (as defined) further including one or more substituents. Additionally, "heteroalkyl" as used herein refers to alkyl groups further containing a heteroatom such as O, P, S, or N.

"Alkenyl" as used herein refers to alkyl groups further containing one or more carbon-carbon double bonds.

Most typically, $R_1$ is hydrogen and $R_2$ is methyl. In one embodiment where $R_1$ is hydrogen and $R_2$ is methyl, $R_3$ is 2-hydroxy heptane as shown below in formula II:

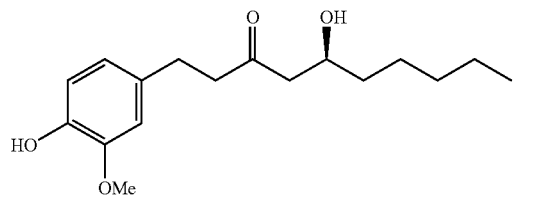

(II)

The compound depicted in formula II is (5S)-5-hydroxy-1-(4-hydroxy-3-methoxyphenyl)-3-decanone, also known as 6-gingerol. Although the S enantiomer is shown above, both racemic mixtures and isolated, optically active enantiomers (R, S) are contemplated for use in the compositions and methods of the invention when molecules have a stereocenter. Additionally, other gingerol structures (e.g., 8-gingerol) may be present in, or prepared from (i.e., synthetically derived from), the extract products in accordance with the invention.

In another embodiment where $R_1$ is hydrogen and $R_2$ is methyl, $R_3$ is heptane as shown in formula III:

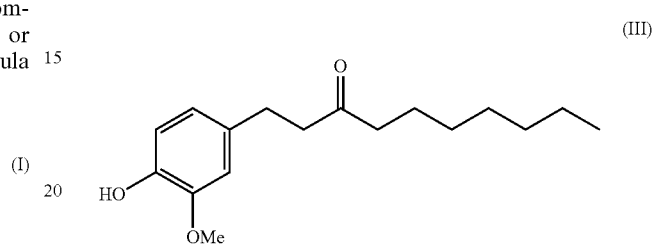

(III)

The compound depicted in formula III is 1-(4-hydroxy-3-methoxyphenyl)-3-decanone, also known as 6-paradol. Additionally, other paradol structures (e.g., 8-paradol) may be present in, or prepared from, the extract products in accordance with the invention.

In yet another embodiment where $R_1$ is hydrogen and $R_2$ is methyl, $R_3$ is hepta-1-ene as shown in formula IV:

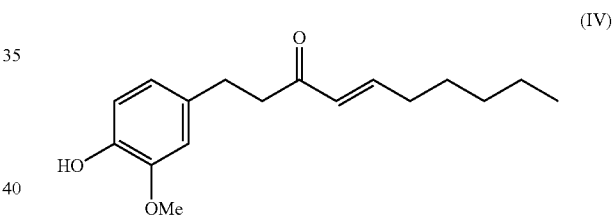

(IV)

The compound depicted in formula IV is 1-(4-hydroxy-3-methoxyphenyl)-deca-4-ene-3-one, also known as 6-shogaol. Additionally, other shogaol structures may be present in, or prepared from, the extract products in accordance with the invention.

The disclosed hypoglycemic compositions typically contain a mixture of compounds in accordance with formulas (I), (II), (III), and/or (IV). Accordingly, the invention contemplates mixtures, which may exhibit additive, or preferably synergistic, effects.

*Aframomum melegueta* plants are grown and harvested using well-known methods. For example, the plants may be grown in an agricultural field. More preferably, the plants are grown in environmentally controlled hydroponic greenhouses using standard hydroponic methods. Hydroponic methods facilitate the reproducible optimization of plant growing conditions, and the optimization of hypoglycemic compound content. Hydroponic methods also facilitate harvesting of the plants. Additionally, controlled growth conditions are advantageous in that they facilitate the standardization of any final product.

The conditions under which the plants are grown may also affect the content of hypoglycemic compounds present therein. In particular, plants subjected to stress conditions, such as heat stress, dehydration, and/or exposure to chemical elicitors, are expected to have a higher hypoglycemic compound content than plants not subjected to such conditions. Any conventionally known chemical elicitor can be used during cultivation of the *Aframomum melegueta* plants, in accordance with known application schedules.

As previously described, the hypoglycemic compounds are typically isolated by extracting plant material of an *Aframomum melegueta* plant. Any plant material, including leaves, stems, flowers, fruits, roots, and combinations thereof, can be extracted. In one embodiment, the above-ground plant parts are extracted. In a further embodiment, the seeds are used (by themselves).

One exemplary extraction method for obtaining high yields of hypoglycemic compounds from *Aframomum melegueta* plants in accordance with the invention comprises the following steps: (1) providing fresh or fresh-frozen plant material; (2) disrupting the plant material; (3) extracting the plant material in a solution containing a sufficient amount of fluid; and (4) collecting the fluid to obtain an extract product. The hypoglycemic extract product may be further processed by: (5) removing solid matter from the extract; (6) removing fluid components; (7) resuspending the resulting residue in an aqueous solution; and (8) after removing any water insoluble material, repeating step (6) to form a more purified form of an extract product. In various embodiments, the plant material can be disrupted by macerating, grinding, or otherwise disrupting the plant material.

In a preferred embodiment, fresh plant tissue is quick-frozen in liquid nitrogen, then ground or otherwise macerated (e.g., using a Polytron or a Waring blender) in fluid. After solids are removed from the extract, e.g., by filtration, centrifugation, or any method known in the art, the hypoglycemic compound content of the extract can optionally be measured by any known method, including spectrometric methods.

Fluids for use in the extraction methods of the invention may be solvents. Suitable fluids include, but are not limited to, water, alcohols, alkanes, halocarbons, ethers, aromatic solvents, ketones, aqueous solutions, and super critical fluids. In one embodiment, ethanol is a preferred alcohol for practice of the invention. A benefit of incorporating an ethanolic fluid in the final extraction step is that an ethanolic fluid is compatible with an ingestible product, and therefore is suitable for incorporation into a pill, capsule, tablet, and other ingestible forms known in the art.

As previously indicated, the hypoglycemic compositions may be formulated as pharmaceutical compositions (e.g., an ethical drug), nutraceutical compositions (e.g., a dietary supplement), compositions for topical administration including, but not limited to, cosmeceuticals (e.g., a cosmetic product having biologically active ingredients), or as a food or beverage additive as defined by the U.S. Food and Drug Administration. In one embodiment, the hypoglycemic compositions include at least one formulation agent selected from the group consisting of diluents, fillers, salts, binders, and biologically acceptable carriers.

Hypoglycemic compositions comprising a hypoglycemic extract product can be tabletted, encapsulated, or otherwise formulated for oral administration (e.g., in a gum or candy). Compositions formulated for oral administration typically include one or more suitable diluents, fillers, salts, disintegrants, binders, lubricants, glidants, wetting agents, controlled release matrices, colorants, flavorings, carriers, excipients, buffers, stabilizers, solubilizers, commercial adjuvants, and/or other additives known in the art.

Any pharmaceutically acceptable (i.e., sterile and acceptably non-toxic, as known in the art) liquid, semisolid, or solid diluent that serves as a pharmaceutical vehicle, excipient, or medium can be used. Exemplary diluents include, but are not limited to, polyoxyethylene sorbitan monolaurate, magnesium stearate, calcium phosphate, mineral oil, cocoa butter, oil of theobroma, methyl- and propylhydroxybenzoate, talc, alginates, carbohydrates, especially mannitol, α-lactose, anhydrous lactose, cellulose, sucrose, dextrose, sorbitol, modified dextrans, gum acacia, and starch. Such additives may influence the physical state, stability, rate of in vivo release, and rate of in vivo clearance of the hypoglycemic compositions.

Pharmaceutically acceptable fillers can include, for example, lactose, microcrystalline cellulose, dicalcium phosphate, tricalcium phosphate, calcium sulfate, dextrose, mannitol, sucrose, and others known in the art. Salts, including calcium triphosphate, magnesium carbonate, and sodium chloride, may also be used as fillers in the pharmaceutical compositions.

Binders may be used to hold the composition comprising the hypoglycemic extract product together to form a hard tablet. Exemplary binders include materials from natural products such as acacia, tragacanth, starch and gelatin. Other suitable binders include methyl cellulose (MC), ethyl cellulose (EC), and carboxymethyl cellulose (CMC).

Hypoglycemic compositions comprising a hypoglycemic extract product can be formulated as sprays, drops, suppositories, transdermal patches, or otherwise formulated for topical administration. Hypoglycemic compositions formulated for topical administration typically include biologically acceptable carriers (i.e., a carrier that does not interfere with the hypoglycemic activity of the *Aframomum melegueta*-derived hypoglycemic extract product). Suitable biologically acceptable carriers are well known in the art and include, but are not limited to, oils and esters. Specific examples include mineral oil, glyceryl stearate, stearic acid, glycerin, silicone 1401, and propylene glycol.

Additionally, cosmeceutical compositions of the present invention can include a wide range of additional components. The CTFA Cosmetic Ingredient Handbook, Second Edition, 1992, which is incorporated by reference herein in its entirety, describes a wide variety of cosmetic and pharmaceutical ingredients commonly used in the skin care industry, which are suitable for use in the compositions of the present invention. Nonlimiting examples of functional classes of ingredients are described at page 537 of this document. Examples of these functional classes include: absorbents, abrasives, anti-acne agents, anticaking agents, antifoaming agents, antimicrobial agents, antioxidants, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, plasticizers, preservatives, propellants, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), sunscreen agents, ultraviolet light absorbers, and viscosity increasing agents (aqueous and nonaqueous). Examples of other functional classes of materials useful herein that are well known to one of ordinary skill in the art include emulsifiers, sequestrants, skin sensates, and the like.

As set forth in Examples 2 and 3, methods in accordance with the invention have been used to measurably and safely reduce elevated glucose levels. The methods for reducing elevated glucose levels include administering to an individual a therapeutically effective amount of a composition comprising a hypoglycemic extract product of a plant material of an *Aframomum melegueta* plant.

The compositions (and thus the methods) of the invention can be used alone or in conjunction with other therapies including, for example, administration of other therapeutic agents (including other hypoglycemic compositions or formulations).

It will be appreciated that the treatment methods of the invention are useful in the fields of human medicine and veterinary medicine. Thus, the subject or individual to be treated may be a mammal, preferably human, or other animals. For veterinary purposes, subjects include, for example, farm animals such as cows, sheep, pigs, horses, and goats; companion animals such as dogs and cats; exotic and/or zoo animals; laboratory animals including mice, rats, rabbits, guinea pigs, and hamsters; and poultry such as chickens, turkeys, ducks, and geese.

One aspect of the invention provides a use for the hypoglycemic extract product or biologically active compositions or compounds derived therefrom in preparing medicaments for the treatment or prevention of the disorders disclosed herein. Again, as previously indicated, prophylactic use is contemplated where one or more CVD risk factors or metabolic syndrome risk factors are present.

In the methods according to the invention, the hypoglycemic compositions may be administered by any known route of administration. For example, a composition comprising a hypoglycemic extract product of an *Aframomum melegueta* plant can be formulated for injection, or for oral, nasal, transdermal or other forms of administration. Typically, the hypoglycemic compositions are formulated for oral or topical administration. In some embodiments, the hypoglycemic compositions are prepared using a non-toxic alcohol or an aqueous solution.

A typical treatment course may comprise administration of multiple doses on a daily basis of a composition comprising an amount of a hypoglycemic extract product effective to decrease circulating glucose levels in an individual. Such a treatment course may be continued for significant periods of time, for example, three doses per day over three months or even indefinitely. In one embodiment, a presently preferred dosing schedule is one dose per day. The treatment may be continued on an as-needed basis.

Additionally, the compositions may be administered to an individual at any time of day. Typically, the compositions are administered at least one hour before consumption of food is anticipated, but the compositions may also be administered after consumption of food.

Of course, the foregoing are only exemplary treatment schedules, and other schedules are contemplated. In each case, the suitability of such schedules and the aforementioned modes of administration are determined by those of skill in the art, using routine procedures. For example, those of skill in the art will be able to take the information disclosed in this specification and optimize treatment regimes for human subjects based on clinical trials performed in accordance with the specification.

EXAMPLES

The following examples are provided to describe the invention in greater detail, and are intended to illustrate, not to limit, the appended claims. Example 1 provides an exemplary method for preparing a hypoglycemic extract product of *Aframomum melegueta*. Examples 2 and 3 provide in vivo evidence that hypoglycemic compositions, each comprising a hypoglycemic extract product of *Aframomum melegueta*, reduce circulating glucose levels. Example 4 describes exemplary methods for purifying and preparing a hypoglycemic extract product, and provides data concerning individual compounds isolated therefrom.

Example 1

Method of Extracting an *A. melegueta* Plant Material

A hypoglycemic extract product was prepared by extracting dry, ground seeds of *Aframomum melegueta* (grains of paradise) in 95 vol. % ethanol in about one part weight (grams of ground seeds) to about 10 parts volume (milliliters of solvent) ratio for 24 hours at room temperature. During the extraction process, a platform shaker was used to continuously agitate the ethanolic fluid to facilitate complete extraction of the ground seeds. After 24 hours, the fluid was filtered, and removed by rotary evaporation to provide an *Aframomum melegueta* extract product.

Example 2

Demonstration of Hypoglycemic Activity of an *A. melegueta* Extract Product on Fasting Glucose Levels The *Aframomum melegueta*-derived hypoglycemic extract product of Example 1 was tested in vivo for hypoglycemic activity.

Animals and Diet

Five week old male C57BL/6 mice (Jackson Laboratories, Bar Harbor, Me.) were placed on either low fat or high fat rodent diets (D12450B, 10% kcal, low fat or D12492, 60% kcal, high fat, Research Diets, New Brunswick, N.J.).

The mice were housed four to a cage under controlled temperature (70° C.) and 12 hr light-dark cycles. Food (standard mouse chow, Purina) and water were available on an ad libitum basis for 7 days. The mice were then randomly divided into six groups (n=6) for the study. Five groups of mice were fed the high fat diet for 12 weeks (Groups 1-5), and the sixth group (Group 6) was fed the low fat diet for 12 weeks. Weekly food intake per cage and individual body weights were determined throughout the study.

Fasting Blood Glucose Levels

After 12 weeks, all mice (Groups 1-6) were fasted for 4 hrs. After fasting, Group 1 mice provided a control and were gavaged with saline containing 5% DMSO; mice of Groups 2-4 were gavaged with different concentrations of the hypoglycemic extract product of Example 1 in 5% DMSO; and, Group 5 mice were gavaged with 300 mg/kg of Metformin in 5% DMSO as a positive control. Group 6 mice, which were fed a low fat diet, were gavaged with saline containing 5% DMSO and thus were also used as a control. Blood glucose levels were measured with a One Touch® Ultra® handheld glucometer (Lifescan, Milpitas, Calif.) using One Touch® Ultra® test strips. Mice were deprived of food during testing and the blood glucose levels of whole blood (obtained from a tail nick procedure) were determined at certain times (0, 3, and 5 hours after fasting commenced).

Results

Groups 1-5 were gavaged with compositions comprising 125, 250, 500 mg/kg of the hypoglycemic extract product of Example 1, and 300 mg/kg of metformin, respectively. The blood glucose levels were tested immediately after treatment (0 hours) and then 3 and 5 hours after treatment. Extract products of *Amomum melegueta* exhibited significant hypoglycemic activity at all concentrations tested with blood glucose levels 3 and 5 hours after the application.

The results of the studies are shown in Table 1, below, and demonstrate significant hypoglycemic activity for the *Aframomum melegueta* extract products. Importantly, each group of animals that received an *Aframomum melegueta* extract product exhibited a significantly greater reduction in glucose levels relative to the relevant positive control group. Thus, this Example demonstrates that *Aframomum melegueta* extract products possess significant hypoglycemic activity, and effectively reduce glucose levels in individual subjects.

TABLE 1

Effect of *A. melegueta* extract product on blood glucose levels

|  | DMSO, Group 1 | *A. melegueta* extract product, 125 mg, Group 2 | *A. melegueta* extract product, 250 mg, Group 3 | *A. melegueta* extract product, 500 mg, Group 4 | Metformin, 300 mg, Group 5 | Low fat, Group 6 |
|---|---|---|---|---|---|---|
| Time - 0 hours ||||||| 
| Animal 1, glucose (mg/dl) | 218 | 284 | 199 | 400 | 252 | 158 |
| Animal 2, glucose (mg/dl) | 251 | 252 | 295 | 231 | 188 | 142 |
| Animal 3, glucose (mg/dl) | 237 | 231 | 320 | 244 | 194 | 130 |
| Animal 4, glucose (mg/dl) | 247 | 253 | 206 | 216 | 184 | 144 |
| Animal 5, glucose (mg/dl) | 260 | 218 | 214 | 235 | 274 | 123 |
| Animal 6, glucose (mg/dl) | 268 | 238 | 191 | 249 | 219 | 145 |
| Animal 7, glucose (mg/dl) | — | — | — | — | — | 160 |
| Avg. glucose (mg/dl) | 246.8 | 246.0 | 237.5 | 262.5 | 218.5 | 143.1 |
| S.D. | 7.2 | 9.3 | 22.6 | 27.9 | 15.2 | 5.0 |
| Time - 3 hours ||||||| 
| Animal 1, glucose (mg/dl) | 192 | 184 | 167 | 239 | 66 | 124 |
| Animal 2, glucose (mg/dl) | 239 | 228 | 185 | 165 | 148 | 126 |
| Animal 3, glucose (mg/dl) | 218 | 228 | 216 | 165 | 161 | 113 |
| Animal 4, glucose (mg/dl) | 290 | 219 | 169 | 142 | 147 | 94 |
| Animal 5, glucose (mg/dl) | 229 | 172 | 159 | 250 | 157 | 117 |
| Animal 6, glucose (mg/dl) | 198 | 195 | 192 | 246 | 219 | 103 |
| Animal 7, glucose (mg/dl) | — | — | — | — | — | 124 |
| Animal 8, glucose (mg/dl) | — | — | — | — | — | 141 |
| Avg. glucose (mg/dl) | 227.7 | 204.3 | 181.3 | 201.2 | 149.7 | 117.8 |
| S.D. | 14.4 | 9.8 | 8.5 | 20.0 | 20.0 | 6.0 |
| Time - 5 hours ||||||| 
| Animal 1, glucose (mg/dl) | 208 | 189 | 187 | 232 | 145 | 160 |
| Animal 2, glucose (mg/dl) | 243 | 151 | 177 | 152 | 96 | 130 |

TABLE 1-continued

Effect of *A. melegueta* extract product on blood glucose levels

|  | DMSO, Group 1 | *A. melegueta* extract product, 125 mg, Group 2 | *A. melegueta* extract product, 250 mg, Group 3 | *A. melegueta* extract product, 500 mg, Group 4 | Metformin, 300 mg, Group 5 | Low fat, Group 6 |
|---|---|---|---|---|---|---|
| Animal 3, glucose (mg/dl) | 278 | 193 | 195 | 193 | 119 | 129 |
| Animal 4, glucose (mg/dl) | 226 | 223 | 139 | 134 | 124 | 103 |
| Animal 5, glucose (mg/dl) | 236 | 178 | 144 | 221 | 162 | 98 |
| Animal 6, glucose (mg/dl) | 199 | 196 | 178 | 170 | 123 | 100 |
| Animal 7, glucose (mg/dl) | — | — | — | — | — | 119 |
| Animal 8, glucose (mg/dl) | — | — | — | — | — | 179 |
| Average value (mg/dl) | 231.7 | 188.3 | 170.0 | 183.7 | 128.2 | 127.3 |
| S.D. | 11.5 | 9.6 | 9.4 | 15.8 | 9.3 | 12.0 |

Example 3

Demonstration of Hypoglycemic Activity of an *A. melegueta* Extract Product in Diabetic Model The *Aframomum melegueta*-derived hypoglycemic extract product of Example 1 was tested in vivo for hypoglycemic activity using a high fat diet-induced diabetic model.

Animals and Diet

Five week old male C57BL/6 mice (Jackson Laboratories, Bar Harbor, Me.) were placed on either low fat or high fat rodent diets (D12450B, 10% kcal, low fat or D12492, 60% kcal, high fat, Research Diets, New Brunswick, N.J.).

The mice were housed individually under controlled temperature (70° F.) and 12 hr light-dark cycles. Food (standard mouse chow, Purina) and water were available on an ad libitum basis for 7 days. The mice were then randomly divided into control Groups 1 and 6 (n=8-10), treatment Groups 2 and 3 (n=6), and two positive control Groups 4 and 5 (n=6) for the study. The control mice continued to receive either a high fat diet or a low fat diet, and the treatment groups were fed the high fat diet for a 14 week period. Two groups of mice were gavaged with PMI006 at a dose of 500 mg/kg daily. As a positive control, Metformin was administered at a dose of 300 mg/kg in two groups of positive control mice.

Oral Glucose Tolerance Test

An oral glucose tolerance test was performed after seven days of treatment. On the test day, animals were fasted for seven hours and glucose (2.0 g/kg) was then orally administered to them. Blood glucose levels were determined from the tail vein at 0 (before glucose challenge), 30, 60, and 120 min after glucose administration.

Blood glucose levels were measured with a One Touch® Ultra® handheld glucometer (Lifescan, Milpitas, Calif.) using One Touch® Ultra® test strips at time=0 (i.e., before glucose challenge), 30 minutes after, 60 minutes after, and 120 minutes after glucose administration. Mice were deprived of food during testing and the blood glucose levels of whole blood (obtained from a tail nick procedure) were determined at certain times. The *Aframomum melegueta*-derived hypoglycemic extract product of Example 1 was orally administered at a dosage of 500 mg/kg to the two treatment Groups 2 and 3 either 1.5 or 3.0 hours before the glucose challenge. Metformin was orally administered at a dosage of 300 mg/kg to the animals in the positive control Groups 4 and 5 either 1.5 or 3.0 hours before the glucose challenge.

The results of the studies are shown in Table 2, below, and demonstrate significant hypoglycemic activity for the *Aframomum melegueta* extract products. Importantly, each group of animals that received an *Aframomum melegueta* extract product exhibited a significantly greater reduction in glucose levels relative to the relevant positive control group.

This Example demonstrates that *Aframomum melegueta* extract products possess significant hypoglycemic activity, and effectively reduce glucose levels in individual subjects.

TABLE 2

Effect of *A. melegueta* extract product on blood glucose levels after 1 wk

| Treatment, measurement time | Group, Number of mice | Plasma glucose (mg/dl) | p-value v. DMSO |
|---|---|---|---|
| DMSO | Group 1, 10 mice | | |
| 0 min | | 212 ± 14.4 | N.A. |
| 30 min | | 392 ± 34.1 | N.A. |
| 60 min | | 327 ± 28.1 | N.A. |
| 90 min | | 213 ± 16.1 | N.A. |
| hypoglycemic extract product, 1.5 hr | Group 2, 6 mice | | |
| 0 min | | 190 ± 11.6 | 0.3412 |
| 30 min | | 302 ± 28.5 | 0.3996 |
| 60 min | | 226 ± 11.2 | 0.4389 |
| 90 min | | 192 ± 11.5 | 0.4176 |
| hypoglycemic extract product, 3 hr | Group 3, 6 mice | | |
| 0 min | | 204 ± 13.4 | 0.1505 |
| 30 min | | 379 ± 37.6 | 0.0425 |

TABLE 2-continued

Effect of *A. melegueta* extract product on blood glucose levels after 1 wk

| Treatment, measurement time | Group, Number of mice | Plasma glucose (mg/dl) | p-value v. DMSO |
|---|---|---|---|
| 60 min | | 321 ± 27.4 | 0.0082 |
| 90 min | | 207 ± 24.6 | 0.1846 |
| Metformin 1.5 hr | Group 4, 6 mice | | |
| 0 min | | 160 ± 4.9 | 0.041 |
| 30 min | | 235 ± 12.2 | 0.0009 |
| 60 min | | 190 ± 11.1 | 0.0005 |
| 90 min | | 164 ± 6.0 | 0.0109 |
| Metformin 3 hr | Group 5, 6 mice | | |
| 0 min | | 173 ± 13.2 | 0.0133 |
| 30 min | | 207 ± 26.7 | 0.0035 |
| 60 min | | 171 ± 14.8 | 0.0025 |
| 90 min | | 158 ± 6.7 | 0.028 |
| low fat diet | Group 6, 8 mice | | |
| 0 min | | 164 ± 6.5 | 0.0058 |
| 30 min | | 256 ± 17.1 | 0.002 |
| 60 min | | 247 ± 20.8 | 0.0205 |
| 90 min | | 171 ± 11.9 | 0.0285 |

Example 4

Methods for Purifying an *A. melegueta* Extract Product

This example describes several exemplary methods for purifying an *Aframomum melegueta* extract product.

LC-MS Gradient (Method A):

Substances were separated on a Phenomenex® Luna C-8 reverse phase column, size 150×2 mm, particle size 3 μm, pore size 100 Å, equipped with a Phenomenex® Security-Guard™ pre-column. The mobile phase consisted of 2 components: solvent A (0.5 vol. % ACS grade acetic acid in double-distilled de-ionized water, pH 3-3.5) and solvent B (100 vol. % acetonitrile). The mobile phase flow was adjusted to 0.25 ml/min, and generally a gradient mode was used as follows: 0-35 min: 95 vol. % solvent A-5 vol. % solvent A; 35-40 min: 5 vol. % solvent A; 40-45 min: 5 vol. % solvent A-95 vol. % solvent A (the balance of the mobile phase was solvent B).

HPLC Fractionation Procedure (Method B):

Compounds were separated on a Waters Symmetry Prep® RP 7 column, size 300×19 mm, particle size 7 μm. The mobile phase consisted of 2 components: solvent A (0.5 vol. % ACS grade acetic acid in double-distilled de-ionized water, pH 3-3.5), and solvent B (100 vol. % acetonitrile). The mobile phase flow was adjusted to 8 ml/min, and generally a gradient mode was used as follows: 0-35 min: 95 vol. % solvent A-5 vol. % solvent A; 35-40 min: 5 vol. % solvent A; 40-50 min 5 vol. % solvent A-95 vol. % solvent A (the balance of the mobile phase was solvent B).

The most prominent peaks were collected so that the fractions could be structurally analyzed by LC-MS. The LC-MS data demonstrated that members of the arylheptanoid family such as gingerols, shogaols and paradols are present in the hypoglycemic extract product (along with other arylheptanoids).

The paradol fraction was subjected to further fractionation.

HPLC Subfractionation Procedure (Method C):

The paradol fraction obtained using Method B was further separated on a Phenomenex® Curosil PFP column, size 250× 4.60 mm, particle size 5 μm. The mobile phase consisted of 2 components: solvent A (double-distilled de-ionized water), and solvent B (100 vol. % acetonitrile). The mobile phase flow was adjusted to 0.5 ml/min, and generally an isocratic mode was used for all analyses as follows: 0-50 min: 40 vol. % solvent A-60 vol. % solvent B.

Subfractionation of the paradol fraction resulted in four major peaks. LC-MS structural analyses of these four peaks established that peaks 1 and 2 have an identical fragmentation pattern that corresponds to [6]-paradol. Peaks 3 and 4 are complex mixtures and were not fully resolved.

The invention is not limited to the embodiments described and exemplified above, but rather is capable of variation and modification without departure from the scope of the appended claims.

What is claimed is:

1. A method of reducing glucose levels, comprising:
   administering a therapeutically effective amount of a composition comprising a hypoglycemic extract of a plant material of an *Aframomum melegueta* plant to an individual desirous of having a reduced glucose level, wherein the hypoglycemic extract comprises a mixture of compounds in accordance with the following formula (I):

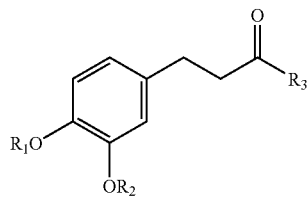

wherein $R_1$ is hydrogen or a $C_1$-$C_4$ moiety;
$R_2$ is hydrogen or a $C_1$-$C_4$ moiety; and,
$R_3$ is a $C_1$-$C_{10}$ moiety.

2. The method of claim 1, wherein the plant material is selected from the group consisting of leaves, stems, flowers, fruits and roots.

3. The method of claim 1, wherein the hypoglycemic extract comprises at least one compound in accordance with the following formula (II):

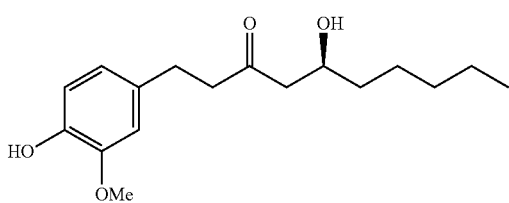

4. The method of claim 1, wherein the hypoglycemic extract comprises at least one compound in accordance with the following formula (III):

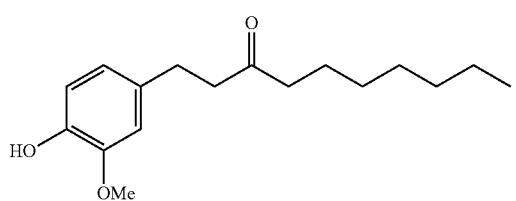

5. The method of claim 1, wherein the hypoglycemic extract comprises at least one compound in accordance with the following formula (IV):

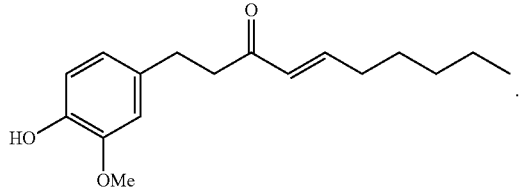

(IV)

6. The method of claim 1, wherein the individual is a mammal.

7. The method of claim 1, wherein the individual has one or more risk factors selected from the group consisting of abdominal obesity, atherogenic dyslipidemia, raised blood pressure, proinflammatory conditions, and prothrombotic conditions.

8. The method of claim 1, wherein the individual has a condition selected from the group consisting of Type I diabetes, Type II diabetes, pre-diabetes, and gestational diabetes.

9. The method of claim 1, wherein the individual has a family history indicating an increased risk of developing Type I diabetes, Type II diabetes, pre-diabetes, or gestational diabetes.

10. The method of claim 1, wherein the individual has family history indicating an increased risk of developing both cardiovascular disease and conditions involving elevated glucose levels.

* * * * *